(12) United States Patent
Iwamoto

(10) Patent No.: US 7,892,284 B2
(45) Date of Patent: Feb. 22, 2011

(54) INTRAOCULAR LENS AND PROCESS FOR PRODUCING THE SAME

(75) Inventor: Hidetoshi Iwamoto, Fukaya (JP)

(73) Assignee: Hoya Corporation, Tokyo (JP)

( * ) Notice: Subject to any disclaimer, the term of this patent is extended or adjusted under 35 U.S.C. 154(b) by 142 days.

(21) Appl. No.: 11/885,221

(22) PCT Filed: Jan. 31, 2006

(86) PCT No.: PCT/JP2006/001941

§ 371 (c)(1),
(2), (4) Date: Sep. 11, 2007

(87) PCT Pub. No.: WO2006/092926

PCT Pub. Date: Sep. 8, 2006

(65) Prior Publication Data

US 2008/0177384 A1    Jul. 24, 2008

(30) Foreign Application Priority Data

Feb. 28, 2005  (JP) .............................. 2005-054421

(51) Int. Cl.
*A61F 2/16*  (2006.01)

(52) U.S. Cl. .................. 623/6.62; 623/6.11; 427/2.24; 424/427

(58) Field of Classification Search ....... 623/6.11–6.64; 427/2.24; 424/427

See application file for complete search history.

(56) References Cited

U.S. PATENT DOCUMENTS

| | | | | |
|---|---|---|---|---|
| 5,002,571 A | * | 3/1991 | O'Donnell et al. | ......... 623/6.11 |
| 5,376,116 A | * | 12/1994 | Poler | .................. 623/6.16 |
| 6,169,127 B1 | * | 1/2001 | Lohmann et al. | ............ 523/106 |
| 6,251,964 B1 | * | 6/2001 | Porssa et al. | ................ 523/105 |
| 2001/0003162 A1 | * | 6/2001 | Chan et al. | .................. 623/6.23 |
| 2001/0037150 A1 | | 11/2001 | Chan et al. | |
| 2003/0186825 A1 | | 10/2003 | Mitani et al. | |
| 2008/0248972 A1 | * | 10/2008 | Nishizawa et al. | ............ 506/32 |

FOREIGN PATENT DOCUMENTS

| | | |
|---|---|---|
| EP | 489185 B1 * | 6/1996 |
| EP | 0947205 A2 * | 10/1999 |
| EP | 0 989 138 | 3/2000 |
| EP | 1211268 A1 * | 6/2002 |
| JP | 9-291040 | 11/1997 |
| JP | 2002-511315 | 4/2002 |
| JP | 2004-275386 | 10/2004 |
| WO | 99/52570 | 10/1999 |
| WO | WO 99/52570 | 10/1999 |
| WO | 2005/065733 | 7/2005 |

OTHER PUBLICATIONS

International Search Report for PCT/JP2006/301941 mailed Mar. 14, 2006.

Nishi et al, "Secondary Cataract Inhibiting Effect of Intraocular Lens", Summary of the 15th Europe Intraocular Lens Society Conference, 1997 w/English abstract.

* cited by examiner

*Primary Examiner*—Paul Prebilic
(74) *Attorney, Agent, or Firm*—Nixon & Vanderhye P.C.

(57) ABSTRACT

Provided is an intraocular lens that inhibits secondary cataract which occurs after insertion of an intraocular lens and that is free from the adherence and deposition of a protein, etc., to/on the front surface of the lens, and the intraocular lens has an optic portion with a front surface and a back surface, said front surface and said back surface being different from each other in the property of adhering to a protein and satisfying the relationship of the expression (x), $$PA_F < PA_B \quad (x)$$

wherein $PA_F$ is the property of adherence of said front surface to fibronectin and $PA_B$ is the property of adherence of said back surface to fibronectin in a fibronectin adherence test.

5 Claims, No Drawings

INTRAOCULAR LENS AND PROCESS FOR PRODUCING THE SAME

This application is the U.S. national phase of International Application No. PCT/JP2006/301941, filed 31 Jan. 2006, which designated the U.S. and claims priority to Japanese Patent Application No. 2005-054421, filed 28 Feb. 2005, the entire contents of each of which are hereby incorporated by reference.

TECHNICAL FIELD

The present invention relates to an intraocular lens and a process for producing the same. More specifically it relates to an intraocular lens that is an intraocular lens to be inserted after the extraction of a lens having suffered from cataract, that inhibits secondary cataract which may occur after surgery and that will have little or no fogging which protein, etc., in the aqueous humor may cause on the front surface side of a lens, and a process for producing the above intraocular lens.

BACKGROUND ART

In recent years, with an increase in the population of aged people, the number of aged patients having senile cataract has noticeably increased. The cataract is a disease in which a lens is opacified, and it induces a decrease in the vision and may sometimes deprive a patient of his or her eyesight. For treating a patient with cataract, the opaque lens and cortex are removed and the vision is corrected with an ophthalmic lens or a contact lens, or an intraocular lens is inserted. It is a generally practiced method at present to remove the lens and then fix an intraocular lens in the capsule.

In the above method, however, remaining lens epithelial cells migrate into the posterior lens capsule and proliferate to generate opacification in the posterior capsule region, and the opacification may spread over the optic portion of the intraocular lens and may cause secondary cataract. For treating this secondary cataract after the insertion of an intraocular lens, there is employed a method in which the opacified portion is removed by irradiation with an Nd:YAG laser beam. However, this method has defects that the apparatus therefor is expensive and that the fundus examination, photocoagulation and vitreous body operation are hampered (for example, see NISHI Okihiro, et al., "Secondary Cataract Inhibiting Effect of Intraocular Lens", Summary of the 15th Europe Intraocular Lens Society Conference, 1997).

As other method, there are known a method of treating and preventing secondary cataract by using a medicine (for example, see JP-A-9-291040), a method of forming an intraocular lens whose circumferential portion has sharp edges to inhibit the secondary cataract (for example, see the above Summary of the 15th Europe Intraocular Lens Society Conference) and a method of coating that portion of an intraocular lens which corresponds to the posterior capsule portion with a biocompatible material having a specific composition (for example, see Japanese Translation Version No. 2002-511315 of PCT Application).

Meanwhile, the entire surface of the anterior capsule portion is incised in the surgery for inserting a lens, and the lens front surface inserted is hence exposed to aqueous humor, etc., unlike the lens back surface side. In recent years, it has come to known that the opacification phenomenon also occurs on the lens front surface side.

There has been so far no intraocular lens that not only inhibits secondary cataract but also works to inhibit the opacification phenomenon that occurs on the lens front surface side.

DISCLOSURE OF THE INVENTION

Under the circumstances, it is an object of the present invention to provide an intraocular lens that inhibits secondary cataract that occurs after the insertion of the intraocular lens and that can further inhibit the opacification phenomenon that occurs on the lens front surface.

For achieving the above object, the present inventor has made diligent studies and as a result it has been found that the above object can be achieved by an intraocular lens having an optic portion having a front surface and a back surface, the front and back surfaces being different from each other in the property of adhering to a protein (capability of being adhered to by a protein) and the back surface having the property of higher adherence to fibronectin than the front surface in a fibronectin adhering test, and in particular by an intraocular lens having a one-piece optic portion whose front surface and/or back surface are specifically surface-treated. The present invention has been completed on the above finding.

That is, the present invention provides;

(1) an intraocular lens having an optic portion having a front surface and a back surface, said front surface and said back surface being different from each other in the property of adhering to a protein and satisfying the relationship of the expression (x), $$PA_F < PA_B \tag{x}$$

wherein $PA_F$ is the property of adherence of said front surface to fibronectin and $PA_B$ is the property of adherence of said back surface to fibronectin in a fibronectin adherence test, (2) an intraocular lens as recited in the above (1), wherein the optic portion is a two-piece optic portion formed of a front surface portion and a back surface portion which are bonded to each other, and said front surface portion and said back surface portion are different from each other in the property of adhering to a protein, (3) an intraocular lens as recited in the above (1), wherein the optic portion is formed of one piece in which the front surface or the back surface is surface-treated or both the front surface and the back surface are surface-treated.

(4) an intraocular lens as recited in the above (3), wherein the front surface of the optic portion is a surface-treated front surface coated with a copolymer having a recurring unit of the general formula (I),

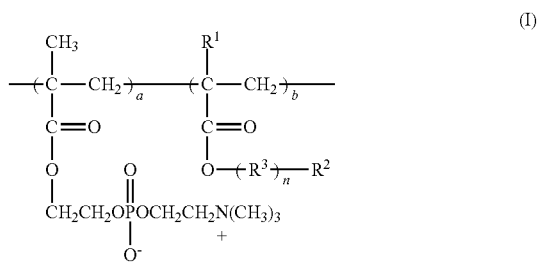

wherein $R^1$ is a hydrogen atom or an alkyl group having 1 to 4 carbon atoms, $R^2$ is a hydrogen atom, a hydroxyl group, a hydrocarbyloxy group, —$Si(OR_4)_3$ in which $R^4$ is a lower alkyl group or trimethylsilyl, or a group represented by

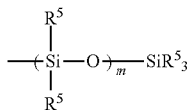

in which $R^5$ is methyl, phenyl or trimethylsiloxy and m is an integer of 1 to 100, $R^3$ is an alkylene group, a is 0.03 to 0.70, b is 0.30 to 0.97 and n is an integer of 2 or more, and having a number average molecular weight of 5,000 or more, the copolymer having been obtained from 2-methacryloyloxyethyl phosphorylcholine and (meth)acrylic ester, (5) an intraocular lens as recited in the above (3), wherein the back surface of the optic portion is surface-treated by plasma treatment and/or by applying active light that works to decompose oxygen molecules to generate ozone and works to decompose said ozone to generate active oxygen in the presence of oxygen, (6) an intraocular lens as recited in the above (3), wherein the front surface of the optic portion is surface-treated with a copolymer having a recurring unit of said general formula (I), having a number average molecular weight of 5,000 or more and having been obtained from 2-methacryloyloxyethyl phosphorylcholine and (meth)acrylic ester, and the back surface of the optic portion is surface-treated by plasma treatment and/or by applying active light that works to decompose oxygen molecules to generate ozone and works to decompose said ozone to generate active oxygen in the presence of oxygen, (7) a process for producing the intraocular lens recited in the above (2), which comprises bonding two lens portions different from each other in the property of adhering to a protein, (8) a process for producing the intraocular lens recited in the above (4), which comprises coating the front surface of an optic portion with a copolymer having a recurring unit of said general formula (I), having a number average molecular weight of 5,000 or more and having been obtained from 2-methacryloyloxyethyl phosphorylcholine and (meth) acrylic ester, thereby to surface-treat the front surface of the optic portion.

(9) a process for producing the intraocular lens recited in the above (5), which comprises surface-treating the back surface of the optic portion by plasma treatment and/or by applying active light that works to decompose oxygen-molecules to generate ozone and works to decompose said ozone to generate active oxygen in the presence of oxygen,

(10) a process for producing the intraocular lens recited in the above (6), which comprises surface-treating the front surface of an optic portion with a copolymer having a recurring unit of said general formula (I), having a number average molecular weight of 5,000 or more and having been obtained from 2-methacryloyloxyethyl phosphorylcholine and (meth) acrylic ester, and surface-treating the back surface of the optic portion by plasma treatment and/or by applying active light that works to decompose oxygen molecules to generate ozone and works to decompose said ozone to generate active oxygen in the presence of oxygen, and

(11) a process for producing the intraocular lens recited in the above (6), which comprises surface-treating the front surface and back surface of an optic portion with a copolymer having a recurring unit of said general formula (I), having a number average molecular weight of 5,000 or more and having been obtained from 2-methacryloyloxyethyl phosphorylcholine and (meth)acrylic ester, and surface-treating the back surface of the optic portion by plasma treatment and/or by applying active light that works to decompose oxygen molecules to generate ozone and works to decompose said ozone to generate active oxygen in the presence of oxygen.

According to the present invention, there can be provided an intraocular lens that is an intraocular lens to be inserted after the extraction of a lens having suffered from cataract, that inhibits secondary cataract which may occur after surgery and that will have little or no fogging on the front surface side of a lens, and a process for producing the same.

PREFERRED EMBODIMENTS OF THE INVENTION

The intraocular lens of the present invention has an optic portion having a front surface and a back surface, said front surface and said back surface being different from each other in the property of adhering to a protein and satisfying the relationship of the expression (x), $$PA_F < PA_B \quad (x)$$

wherein $PA_F$ is the property of adherence of said front surface to fibronectin and $PA_B$ is the property of adherence of said back surface to fibronectin in a fibronectin adherence test.

The intraocular lens of the present invention is a lens to be inserted after the extraction of a lens having suffered from cataract, and it functions to inhibit secondary cataract which may occur after surgery and functions to suppress a fogging on the front surface side of a lens. For exhibiting these functions, the value of $PA_F/PA_B \times 100$ is preferably 50 or less, more preferably 20 or less, still more preferably 10 or less.

The properties of adherence to fibronectin $PA_F$ and $PA_B$ refer to values determined in the following fibronectin adherence test.

<Fibronectin Adherence Test>

Fibronectin (HFN: supplied by Haematologic Technologies Inc.) in an amount of 2 mg is dissolved in 5 ml of pure water, and "Opeguard MA" is added to the solution to prepare a 40 ml solution having a fibronectin concentration of 50 μg/ml. A sample lens is sliced to obtain a front surface portion and a back surface portions as specimens.

These two specimens are transferred into a serum tube, 2 ml of fibronectin solution is added and the tube is hermetically stoppered and shaken with a bioshaker (TAITEC BR-3000LF) at 37° C. for 24 hours. After completion of the shaking, the specimens are taken out, liquid on each lens surfaces is wiped off with Kim Wipe, and the lenses are transferred into glass test tubes and subjected to amino acid analysis.

In the amino acid analysis, 200 μl of 6 mol/L hydrochloric acid is placed in each glass test tube with the test lens in it and the test tubes are stoppered under reduced pressure, followed by hydrolysis at 110° C. for 22 hours. After the hydrolysis, each reaction mixture is died to solidness under reduced pressure, and each residue is separately dissolved in 100 μl of pure water. Each of the resultant solutions is filtered with a 0.22 μm filter, and 50 μl of each filtrate is subjected to amino acid analysis (Hitachi L-8500 amino acid analyzer/ninhydrin color development method) to determine an amount $PA_F$ of fibronectin that adhered to the front surface portion specimen and an amount $PA_B$ of fibronectin that adhered to the back surface portion specimen.

The intraocular lens of the present invention includes the following two lenses, i.e., (1) an intraocular lens having a two-piece optic portion formed of a front surface portion and a back surface portion which are bonded to each other, said front surface portion and said back surface portion being different in the property of adhering to a protein, and (2) an intraocular lens having a one-piece optic portion having a front surface and a back surface, in which the front surface or the back surface is surface-treated or both the front surface and the back surface are surface-treated. Of these intraocular lenses, the above (2) intraocular lens having a one-piece optic portion is more preferred.

The above (1) intraocular lens having a two-piece optic portion can be obtained by bonding two lens portions that are different from each other in the property of adhering to a protein. That is, it can be obtained by bonding the two lens portions to each other such that the two lens portions satisfy the relationship of the expression (x), $$PA_F < PA_B \qquad (x)$$

wherein $PA_F$ is the property of adherence of the lens portion on the front surface to fibronectin and $PA_B$ is the property of adherence of the lens portion on the back surface to fibronectin. As a method for the above bonding, a known method conventionally used for bonding lens portions, i.e., a method using an adhesive or a melt-fusing method can be employed.

The front surface lens portion and the back surface lens portion are preferably those lens portions which are different from each other in the property of adhering to a protein. The above (1) intraocular lens having a two-piece optic portion can be also obtained in a manner in which the front surface lens portion is treated, for example, to ensure that the adherence thereof to a protein is inhibited as will be described later and the back surface portion is treated, for example, to ensure that the adherence thereof to a protein is improved as will be described later.

The above (2) intraocular lens having a one-piece optic portion preferably includes intraocular lenses according to the following three embodiments.

The intraocular lens according to the first embodiment is an intraocular lens having an optic portion whose front surface is surface-treated to inhibit the property of adhering to a protein, by coating the front surface of the optic portion with a copolymer having a recurring unit of the above general formula (I), having a number average molecular weight of 5,000 or more and having been obtained from 2-methacryloyloxyethyl phosphorylcholine and (meth)acrylic ester, the optic portion satisfying the relationship of the above expression (x).

The intraocular lens according to the second embodiment is an intraocular lens having an optic portion whose back surface is surface-treated to be improved in the property of adhering to a protein by plasma treatment and/or by applying active light that works to decompose oxygen molecules to generate ozone and works to decompose said ozone to generate active oxygen in the presence of oxygen, the optic portion satisfying the relationship of the above expression (x).

The intraocular lens according to the third embodiment is an intraocular lens having an optic portion whose front surface is surface-treated to inhibit the property of adhering to a protein, by coating the front surface of the optic portion with the above copolymer and whose back surface is surface-treated to be improved in the property of adhering to a protein by plasma treatment and/or by applying active light that works to decompose oxygen molecules to generate ozone and works to decompose said ozone to generate active oxygen in the presence of oxygen, the optic portion satisfying the relationship of the above expression (x).

It should be understood that the intraocular lens according to the third embodiment includes an intraocular lens having an optic portion whose front surface and back surface are surface-treated by coating these surfaces with the above copolymer and whose back surface is then surface-treated by plasma treatment and/or by applying active light that works to decompose oxygen molecules to generate ozone and works to decompose said ozone to generate active oxygen in the presence of oxygen.

In the present invention, of the intraocular lens according to the above three embodiments, the intraocular lens according to the third embodiment is particularly preferred.

In the above first and third embodiments, the treatment of the front surface of the optic portion to inhibit the property of adhering to a protein uses a copolymer (to be sometimes simply referred to as "copolymer" hereinafter) having a recurring unit of the above general formula (I),

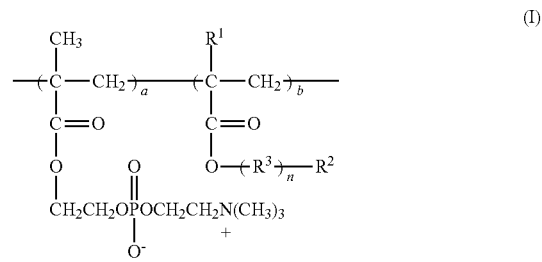

and having been obtained from 2-methacryloyloxyethyl phosphorylcholine and (meth)acrylic ester.

In the above general formula (I), $R^1$ is a hydrogen atom or an alkyl group having 1 to 4 carbon atoms. The alkyl group having 1 to 4 carbon atoms includes methyl, ethyl, n-propyl, isopropyl, n-butyl, isobutyl, sec-butyl and tert-butyl.

$R^2$ is hydrogen atom, a hydroxyl group, a hydrocarbyloxy group, $-Si(OR^4)_3$ in which $R^4$ is a lower alkyl group or trimethylsilyl, or a group represented by

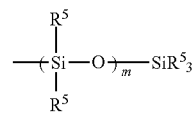

in which $R^5$ is methyl, phenyl or trimethylsiloxy and m is an integer of 1 to 100.

The above hydrocarbyloxy group includes alkoxyl groups such as methoxy, ethoxy, n-propoxy, isopropoxy, various butoxy groups, various pentoxy groups, various hexoxy groups, cyclohexyloxy, various dodecyloxy groups, various hexadecyloxy groups and various octadecyloxy groups, aryloxy groups such as phenoxy, naphthyloxy and anthryloxy, and aralkyloxy groups such as benzyloxy and phenethyloxy. Further, lower alkyl group or groups or halogen atom or atoms may be substituted on the aromatic ring of each of the above aryloxy groups and aralkyloxy groups.

The lower alkyl group represented by $R^4$ includes methyl, ethyl, n-propyl, isopropyl and various butyl groups. $-Si(OR^4)_3$ is preferably trimethoxysilyl, in which $R^4$ is methyl.

Further, $R^5$ is methyl, phenyl or trimethylsiloxy, and methyl or trimethylsiloxy is preferred.

In the above general formula (I), $R^3$ is an alkylene group, and the alkylene group may be linear or branched. Specifically, the alkylene group includes a methylene group, an ethylene group, a trimethylene group, tetramethylene group and any one of these groups having, as a side chain, at least one alkyl group selected from methyl, ethyl, n-propyl, isopropyl or various butyl groups.

In the above general formula (I), n is an integer of 2 or more, and in view of solubility in a polar solvent when the copolymer is used as a material for coating the intraocular lens, n is preferably 2 to 5. Further, when the copolymer has the above general formula (I) in which $R^1$ is methyl, $R^2$ is a hydrogen atom, $R^3$ is a methylene group and n is 4, the copolymer exhibits an excellent effect on the inhibition of the property of adhering to a protein.

In the above general formula (I), further, a is 0.03 to 0.70 and b is 0.30 to 0.97. When a and b are in the above ranges, the copolymer exhibits an excellent effect on the inhibition of the property of adhering to a protein. Preferably, a is 0.10 to 0.60 and b is 0.40 to 0.90.

The copolymer having the recurring unit of the above general formula (I) has a number average molecular weight of at least 5,000, and the number average molecular weight thereof is preferably 50,000 to 2,000,000, particularly preferably 200,000 to 800,000. When the above number average molecular weight is in the above range, the above copolymer has excellent film formability and permits uniform coating when it is coated on a lens, and a coating film having high strength can be formed. The above number average molecular weight refers to a value obtained, as polymethyl methacrylate, by measurement according to a gel permeation chromatography (GPC) method.

The copolymer having the recurring unit of the above general formula (I), used in the present invention, can be produced by copolymerizing 2-methacryloyloxyethyl phosphorylcholine (to be sometimes abbreviated as "MPC" hereinafter) of the general formula (II) and a (meth)acrylic ester of the following general formula (III) in a solvent in the presence of a polymerization initiator.

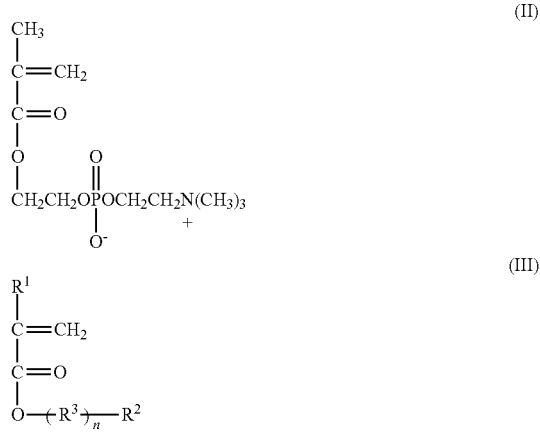

In the formulae, $R^1$, $R^2$, $R^3$ and n are as defined hereinabove.

MPC of the above general formula (II) can be obtained, for example, by reacting 2-bromoethylphosphoryl-dichloride with 2-hydroxyethyl methacrylate to obtain 2-methacryloyloxyethyl-2'-bromoethylphosphoric acid and then allowing this reaction product to react in a solution of trimethylamine in methanol.

Specific examples of the (meth)acrylic ester of the above general formula (III) include methyl(meth)acrylate, ethyl (meth)acrylate, propyl(meth)acrylate, butyl (meth)acrylate, pentyl(meth)acrylate, hexyl(meth)acrylate, heptyl(meth) acrylate, octyl(meth)acrylate, tridecyl (meth)acrylate, 2-ethoxylhexyl(meth)acrylate, 2-ethoxypropyl(meth)acrylate, 2-phenoxyethyl(meth)acrylate, 2-butoxyethyl(meth) acrylate, 2-hydroxyethyl(meth)acrylate, tris(trimethylsiloxy)-γ-methacryloxypropylsilane, 3-methacryloxypropyltrimethoxysilane, 3-methacryloxypropyltris(methoxyethoxy)silane, 3-methacryloxypropylmethyldiethoxysilane and 3-methacryloxypropylmethyldimethoxysilane. As the above (meth)acrylic ester, it is preferred to use ethyl (meth)acrylate, propyl(meth)acrylate, butyl(meth)acrylate or pentyl(meth)acrylate, and above all, it is particularly preferred to use butyl(meth)acrylate for attaining an excellent effect on the inhibition of adherence to a protein. The above (meth)acrylic esters may be used singly or in combination.

The amounts of the above MPC and the (meth)acrylic ester are adjusted to ensure that there is obtained a copolymer of the above general formula (I) in which a is 0.03 to 0.70 and b is 0.30 to 0.97, preferably, a is 0.10 to 0.60 and b is 0.40 to 0.90.

For the polymerization, a known method can be employed. As a solvent, any solvent can be used so long as it can dissolve the monomers. For example, the solvent can be selected from water, methanol, ethanol, propanol, t-butanol, benzene, toluene, dimethylformamide, tetrahydrofuran, chloroform or any mixture of these.

As a polymerization initiator, any polymerization initiator can be used if it is a general radical polymerization initiator. For example, the polymerization initiator can be selected from aliphatic azo compounds such as 2,2'-azobisisobutyronitrile, azobisvaleronitrile, etc., and organic and inorganic peroxides such as benzoyl peroxide, lauroyl peroxide, ammonium persulfate, potassium persulfate, etc.

In the above manner, the copolymer having the recurring unit of the above general formula (I) can be obtained.

In the above first and third embodiments of the intraocular lens of the present invention, the front surface of the optic portion is surface-treated by coating the front surface with the above copolymer.

For coating the front surface with the above copolymer, first, a coating solution containing the above copolymer is prepared. The concentration of the coating solution can be determined as required for obtaining a uniform coating film having a desired thickness, and for example, the concentration can be in the range of 0.05 to 1 mass %, preferably 0.1 to 0.3 mass %. When a spin coater is used, a centrifugal force works as the number of revolutions of the spin coater increases, so that the thickness of the coating film decreases. For obtaining the intraocular lens of the present invention, preferably, the number of revolutions of the spin coater and the time period for the spin coating are determined by taking account of a thickness of a desired coating film and the concentration of the coating solution. When a lens is coated with a spin coater after dipped in the coating solution, the number of revolutions of the spin coater can be, for example, 2,000 to 8,000 rpm, and the time period for the spin coating can be, for example, 5 to 30 seconds.

The solvent for the coating solution is not specially limited so long as it can dissolve the above copolymer. For example, it can be selected from ethanol, methanol, propanol or butanol. Of these, ethanol is preferred to use in view of its volatility and safety.

The coating film formed on the front surface of the optic portion preferably has a thickness of 10 nm or more. When the thickness of the coating film is 10 nm or more, the entire front surface of the optic portion can be uniformly coated. The thickness of the coating film is preferably in the range of 12 to 16 nm. The thickness of the coating film can be measured by the following method.

In a method of measuring a thickness of a coating film on a lens per se with an automatic ellipsometer, it is difficult to accurately measure a thickness of a film formed on a transparent substrate or a substrate having a curvature. In the present invention, therefore, a coating film is formed on a silicon wafer instead of a lens, and the coating film is measured for a thickness under predetermined conditions. Specifically, a coating film is formed on a silicon wafer obtained by slicing in a size of 10 mm×10 mm instead of a lens, the coated silicon wafer is set on an automatic ellipsometer and the coating film is measured for a thickness by means of an He—Ne laser having a wavelength of 632.8 nm at an incidence angle of 70°. Nine points on the silicon wafer are measured, and an average of the nine measurement values is taken as a thickness of the coating film.

Further, it can be visually ascertained whether or not the coating film is uniformly formed.

For strengthening the bonding of a lens and the coating film, the lens surface on which the coating film is to be formed may be subjected to ultraviolet ray treatment, plasma treatment, corona discharge treatment or the like. For speeding up the removal of the solvent, a formed coating may be dried under reduced pressure.

In the above second and third embodiments of the intraocular lens of the present invention, the back surface of the optic portion is treated for improving the property of adhering to a protein.

For the treatment to improve the property of adhering to a protein, there can be preferably employed a method in which the back surface of the optic portion is surface-treated by plasma treatment and/or by applying active light that works to decompose oxygen molecules to generate ozone and works to decompose said ozone to generate active oxygen in the presence of oxygen.

In the above plasma treatment, argon gas, helium gas or oxygen gas is preferred as a gas to be used therefor. The plasma treatment can be carried out under atmospheric pressure or reduced pressure, and there is no special limitation to be imposed on an apparatus for the treatment except for the use of a lens-setting tool that ensures the treatment only of the back surface of the lens.

In the treatment with active light that works to decompose oxygen molecules to generate ozone and works to decompose said ozone to generate active oxygen in the presence of oxygen, the active light is preferably light that has two light emission peaks in the region of 150 to 300 nm and that works to decompose oxygen molecules to generate ozone and works to decompose the ozone to generate active oxygen species, and in particular, there can be employed, for example, light having light emission peaks in the wavelength region of 185±5 nm and the wavelength region of 254±5 nm. This active light can be generated, for example, by means of a low-pressure mercury lamp.

In the present invention, for generating active oxygen species, the above active light is applied in the presence of oxygen. This oxygen can be selected from oxygen gas or oxygen-containing gas such as air.

When light having light emission peaks in the wavelength region of 185±5 nm and the wavelength region of 254±5 nm is applied, it is considered that light having a light emission peak in the wavelength region of 185±5 nm first decomposes oxygen molecules to generate ozone and then light having a light emission peak in the wavelength region of 254±5 nm decomposes the above ozone to generate active oxygen species having high energy.

Although not specially limited, conditions for the active light application can be determined as required while taking account of a material constituting the optic portion of an intraocular lens. When the active light has high application intensity, the treatment can be completed in a short period of time. Since, however, such active light induces the deterioration of a lens, it is required to take heed to such. Further, some lens materials are structurally easily decomposable, so that it is desirable to make studies in advance. Further, when the application time period is long, a lens may be colored, and it is hence also required to take heed to such. Desirably, the intraocular lens is cleaned before the application of active light.

As other method, an ion beam application method or a corona discharge treatment method can be also employed.

The back surface of optic portion of the intraocular lens is surface-treated in the above manner, whereby the optic portion is improved in the property of adhering to fibronectin that is an adhering protein, and as a result, the secondary cataract that may occur after surgery can be inhibited.

With regard to the above point, Reijo J. Linnola, et al. suggest that fibronectin plays an important role in the adhering property of optic portion of an intraocular lens (J Cataract Refract Surg 2000; 26: 1792-1806) and that a lens having the property of highly adhering to fibronectin is effective for inhibiting the secondary cataract.

Further, since the front surface of a lens has almost no capability of adhering to a protein, the adhering of a protein, an inorganic salt, etc., in aqueous humor is suppressed, and the transparency of the lens is maintained.

In the present invention, the intraocular lens that is surface-treated is not specially limited, and the intraocular lens includes both a soft lens whose optic portion is foldable and a hard lens whose optic portion is non-foldable. Although not specially limited, the material for the above soft lens or hard lens is preferably an acrylic material.

The acrylic material for the above soft lens includes, for example, a polymer obtained from at least two monomers selected from 2-phenylethyl methacrylate, 3-phenylpropyl methacrylate, 2-phenoxyethyl methacrylate, 2-phenylethyl acrylate, 3-phenylpropyl acrylate, 2-phenoxyethyl acrylate, ethyl acrylate, n-propyl acrylate, isobutyl acrylate, isoamyl acrylate, hexyl acrylate, 2-hydroxy methacrylate, N-vinylpyrrolidone, etc., in the presence of at least one crosslinking agent selected from ethylene glycol di(meth)acrylate, diethylene glycol di(meth)acrylate, triethylene glycol di(meth)acrylate, 1,4-butanediol di(meth)acrylate and 1,6-hexanediol di(meth)acrylate.

The acrylic material for the hard lens includes, for example, a polymer obtained from at least one member selected from methyl methacrylate and ethyl methacrylate.

As an intraocular lens for use in the present invention, a soft lens formed of a soft acrylic material is particularly preferred.

The amount of the crosslinking agent based on the total monomer amount is preferably 0.3 to 5 mass %, particularly preferably 0.5 to 4 mass %. When the amount of the crosslinking agent is less than 0.3 mass %, no sufficient effect by the introduction thereof is exhibited. When it exceeds 5 mass %, the number of crosslinking points increases to make a polymer (lens) fragile, and the mechanical strength of the polymer is decreased. For the polymerization, heat, light, electron beam, etc., can be used. The amount of a polymerization initiator based on the total monomer amount is preferably 0.1 to 2 mass %, particularly preferably 0.2 to 1 mass %.

The form of the intraocular lens is not specially limited. For example, there are a one-piece type in which the optic portion and haptic portions are integrally formed and a three-piece type having haptic portions formed of polypropylene, PMMA or the like.

Further, a monomer having an ultraviolet-absorbing function such as 2-(2-hydroxy-3-tert-butyl-5-methylphenyl)-5-(2-methacryloxyethyl)benzotriazole or the like may be incorporated into the above monomers. The amount of this monomer (having an ultraviolet-absorbing function) based on the total amount of the foregoing monomers is preferably 0.1 to 4 mass %, particularly preferably 0.5 to 2 mass %. For correcting cyanopsia, further, the foregoing monomers may contain a yellow reactive monomer having a yellow chromophore such as 4-(5-hydroxy-3-methyl-1-phenyl-4-pyrazolylmethyl)-3-methacrylamino-1-phenyl-2-pyrazolin-5-one or the like.

In the present invention, the method for producing an intraocular lens which is to be surface-treated is not specially limited, and a conventionally known method can be employed.

Specifically, there may be employed any one of (1) a method in which a plastic disk that is formed of a haptic-portion-forming material and has a concave portion is prepared and monomer(s) for forming an optic portion is charged into the above concave portion and polymerized, followed by cutting and polishing in a predetermined form, to obtain an intraocular lens, (2) a method in which acrylic monomer(s) for forming haptic portions is filled around a rod-shaped plastic member formed of an optic-portion-forming material and polymerized, followed by cutting and polishing in a predetermined form, to obtain an intraocular lens, and (3) a method in which monomer(s) are injected into an intraocular-lens-shaped cavity of a resin mold to integrally form an optic portion and haptic portions from the same material.

In the above (1) method, as a material for forming the above plastic disk that is formed of a haptic-portion-forming material and has a concave portion, polyalkyl methacrylate, a fluorine resin (polyvinylidene fluoride), a polyimide resin, etc., are used.

In the above (2) method, as an acrylic monomer for forming the haptic portions, there are employed monomers that are used for forming the polyalkyl methacrylate described as an example of the material for constituting the above plastic disk that is formed of a haptic-portion-forming material and has a concave portion in the above (1) method.

In the above (3) method, as a monomer for integrally forming the optic portion and the haptic portions, there are employed monomers that are described as examples for obtaining acrylic materials for the above soft lens and hard lens.

EXAMPLES

The present invention will be explained further in detail below with reference to Examples, while the present invention shall not be limited by these Examples.

Tests of lenses obtained in Examples with regard to the inhibition of secondary cataract of a rabbit eye were carried out as follows.

<Test on Inhibition of Secondary Cataract of Rabbit Eye>

[Operation for Implantation in Rabbit Eye]

An eight week old white rabbit (about 2 kg) which had been mydriatic with an ophthalmic drug (trade name: MYDRIN-P™, supplied by Santen Pharmaceutical Co., Ltd.) before surgery was subjected to general anesthesia and subjected to the treatment of ultrasonic emulsification suction and a lens was inserted through a 4.0 mm×4.0 mm corneal incision.

[Preparation of Tissue Sample]

Two weeks after the surgery, the rabbit was euthanized, and an eyeball was extracted and immobilized with 10 wt % formalin. After dehydration, a paraffin section was prepared, subjected to the treatment of paraffin removal and then stained with hematoxylin-eosin. The tissue section was divided into an intraocular lens central portion and a circumferential portion and observed through a biomicroscope ("BX-51" supplied by Olympus Corporation).

Further, the fibronectin adhering test for showing the property of a lens adhering to cells was carried out according to the method described in the present specification.

Example 1

A soft acryl lens having haptic portions formed of PMMA (colored in blue) and an optic portion (capable of absorbing ultraviolet) was produced from compositions shown in Table 1 by a cutting-polishing method.

A very small amount of an ethanol solution containing 0.2 mass % of a copolymer obtained from MPC monomer and n-butyl(meth)acrylate (MPC:n-butyl acrylate=3:7 by molar ratio, number average molecular weight=600,000) was dropped on the front surface of the above soft acryl intraocular lens, and the turning of the lens with a spin coater at a rate of 5,000 rpm for 10 seconds was repeated twice, to give an intraocular lens having an MPC coating film formed on the front surface thereof (coating film thickness: 13 nm). Then, the thus-obtained lens was set on a specialized tool, the tool with the lens on it was placed in a photo surface-treatment experimental apparatus PL16-110 (supplied by SEN LIGHTS CORPORATION) and the back surface of the lens was treated for 180 seconds. The thus-obtained lens was sterilized with EOG (ethylene oxide gas) and used to carry out the fibronectin adhering test and the test using a rabbit eye with regard to inhibition of secondary cataract.

As a result of the fibronectin adhering test, the amount of fibronectin adhering to the front surface (MPC polymer-coated side) was 0.15 μg, and the amount of fibronectin adhering to the back surface (active-light-treated side) was 0.55 μg. Separately, front surface and back surface specimens prepared by cutting a lens that had not been surface-treated were subjected to a similar fibronectin adhering test to show an adhering amount of 0.28 g. It is hence considered that the adhering amount to a non-treated lens is 0.14 μg.

On the basis of the above results, the fibronectin adhering amounts on the front and back surfaces of the treated lens are calculated to show that the adhering amount on the front surface side (MPC polymer coating) is 0.01 μg (0.15 μg−0.14 μg=0.01 μg) or almost no fibronectin adheres. On the other hand, the adhering amount on the back surface side (active-light-treated side) is 0.41 μg (0.55 μg−0.14 μg=0.41 μg).

As described above, the front surface side and the back surface side of the lens showed a remarkably large difference in the property of adhering to fibronectin.

Further, as a result of the test using a rabbit eye with regard to inhibiting secondary cataract, the proliferation of lens epithelial cells was observed in a circumferential portion of the intraocular lens. In the region of the optic portion, however, it was found that lens epithelial cells proliferated to a slight degree but they were of a single layer, so that the occurrence of secondary cataract was clearly inhibited.

Example 2

A soft acryl lens having haptic portions formed of PMMA (colored in blue) and an optic portion (capable of absorbing ultraviolet light) was produced from compositions shown in Table 1 by a cutting-polishing method.

A very small amount of an ethanol solution containing 0.2 mass % of a copolymer obtained from MPC monomer and n-butyl(meth)acrylate (MPC:n-butyl acrylate=3:7 by molar ratio, number average molecular weight=600,000) was dropped on the front surface of the above soft acryl intraocular lens, and the turning of the lens with a spin coater at a rate of 5,000 rpm for 10 seconds was repeated twice, to give an intraocular lens having an MPC coating film formed on the front surface thereof. Then, the above lens was set on a specialized tool, the tool with the lens on it was placed in a plasma apparatus PA100AT supplied by KYOTO ELECTRONICS MANUFACTURING CO., LTD., and the back surface of the lens was plasma-treated with argon gas for 300 seconds (50 W). The thus-obtained lens was sterilized with EOG and used to carry out the fibronectin adhering test and the test using a rabbit eye with regard to inhibition of secondary cataract.

Table 2 shows the results.

Example 3

A yellow soft acryl lens having haptic portions formed of PMMA (colored in blue) and an optic portion (yellow) was produced from compositions shown in Table 1 by a cutting-polishing method.

A very small amount of an ethanol solution containing 0.2 mass % of a copolymer obtained from MPC monomer and n-butyl(meth)acrylate (MPC:n-butyl acrylate=3:7 by molar ratio, number average molecular weight=600,000) was dropped on the front surface of the above soft acryl intraocular lens, and the turning of the lens with a spin coater at a rate of 5,000 rpm for 10 seconds was repeated twice, to give an intraocular lens having an MPC coating film formed on the front surface thereof.

Then, the thus-obtained lens was set on a specialized tool, the tool with the lens on it was placed in a photo surface-treatment experimental apparatus PL16-110 (supplied by SEN LIGHTS CORPORATION) and the back surface of the lens was treated for 180 seconds. The thus-obtained lens was sterilized with EOG and used to carry out the fibronectin adhering test and the test using a rabbit eye with regard to inhibition of secondary cataract.

Table 2 shows the results.

Example 4

A yellow soft acryl lens having an optic portion and haptic portions, which were integrally formed, was produced from a composition shown in Table 1 by a casting method.

A very small amount of an ethanol solution containing 0.2 mass % of a copolymer obtained from MPC monomer and n-butyl(meth)acrylate (MPC:n-butyl acrylate 3:7 by molar ratio, number average molecular weight=600,000) was dropped on the front surface of the above soft acryl intraocular lens, and the turning of the lens with a spin coater at a rate of 5,000 rpm for 10 seconds was repeated twice, to give an intraocular lens having an MPC coating film formed on the front surface thereof. Then, the thus-obtained lens was set on a specialized tool, the tool with the lens on it was placed in a photo surface-treatment experimental apparatus PL16-110 (supplied by SEN LIGHTS CORPORATION) and the back surface of the lens was treated for 180 seconds. The thus-obtained lens was sterilized with EOG and used to carry out the fibronectin adhering test and the test using a rabbit eye with regard to inhibition of secondary cataract.

Table 2 shows the results.

Comparative Example 1

A soft acryl lens having haptic portions formed of PMMA (colored in blue) and an optic portion (capable of absorbing ultraviolet light) was produced from compositions shown in Table 1 by a cutting-polishing method. The thus-obtained lens was sterilized with EOG and used to carry out the fibronectin adhering test and the test using a rabbit eye with regard to inhibition of secondary cataract.

Table 3 shows the results.

In the test using a rabbit eye with regard to inhibition of secondary cataract, the proliferation of lens epithelial cells was observed in a circumferential portion of the lens. And, in the central portion of the lens, lens epithelial cells that proliferated spread between the intraocular lens and a posterior capsule and formed multiple layers and high-degree secondary cataract occurred.

Comparative Example 2

A soft acryl lens having haptic portions formed of PMMA (colored in blue) and an optic portion (capable of absorbing ultraviolet light) was produced from compositions shown in Table 1 by a cutting-polishing method.

Then, the above lens was set on a specialized tool, the tool with the lens on it was placed in a plasma apparatus PA100AT supplied by KYOTO ELECTRONICS MANUFACTURING CO., LTD., and each of the front and back surfaces of the lens was plasma-treated with argon gas for 300 seconds (50 W). The thus-obtained lens was sterilized with EOG and used to carry out the fibronectin adhering test and the test using a rabbit eye with regard to inhibition of secondary cataract.

Table 3 shows the results.

Comparative Example 3

A yellow soft acryl lens having haptic portions formed of PMMA (colored in blue) and an optic portion (yellow) was produced from compositions shown in Table 1 by a cutting-polishing method.

Then, the thus-obtained lens was set on a specialized tool, the tool with the lens on it was placed in a photo surface-treatment experimental apparatus PL16-110 (supplied by SEN LIGHTS CORPORATION) and each of the front and back surfaces of the lens was treated for 180 seconds. The thus-obtained lens was sterilized with EOG and used to carry out the fibronectin adhering test and the test using a rabbit eye with regard to inhibition of secondary cataract.

Table 3 shows the results.

Comparative Example 4

A yellow soft acryl lens having an optic portion and haptic portions, which were integrally formed, was produced from a composition shown in Table 1 by a casting method. The thus-obtained lens was used to carry out the fibronectin adhering test and the test using a rabbit eye with regard to inhibition of secondary cataract.

Table 3 shows the results.

TABLE 1

|  |  | Ex. 1, Ex. 2<br>CEx. 1, CEx. 2 | Ex. 3<br>CEx. 3 | Ex. 4<br>CEx. 4 |
|---|---|---|---|---|
| Composition for | MMA | 98 | 98 | — |
| haptic portions | EDMA | 2 | 2 | — |
| (part by mass, | AIBN | 0.3 | 0.3 | — |
| excluding %) | AQ-1 | 0.06% | 0.06% | — |
| Composition for | PEMA | 52 | 52 | 52 |
| optic portion | n-BA | 42 | 42 | 42 |
| (part by mass, | BRM | 6 | 6 | 6 |
| excluding %) | EDMA | 2 | 2 | 2 |
|  | AIBN | 0.3 | 0.3 | 0.3 |
|  | T-1500 | 1.50% | 1.00% | 1.00% |
|  | HMPO | — | 0.02% | 0.02% |

(% represents a value based on the total monomer mass amount)
(Notes)
MMA: Methyl methacrylate
EDMA: Ethylene glycol dimethacrylate
PEMA: 2-Phenylethyl methacrylate
BRM: Perfluorooctylethyloxypropylene methacrylate
n-BA: n-Butyl acrylate
AIBN: 2,2'-azobis(isobutyronitrile)
T-150: 2-(2-hydroxy-3-tert-butyl-5-methylphenyl)-5-(2-methacryloyloxyethyl)benzotriazole
AQ-1: 1-Anilino-4-(4-vinylbenzyl)aminoanthraquinone
HMPO: 4-(5-Hydroxy-3-methyl-1-phenyl-4-pyrazolylmethylene)-3-methacrylamino-1-phenyl-2-pyrazolin-5-one

TABLE 2

| | Method of surface treatment | | Amount of adhering fibronectin | | Thickness of adhering epithelial cells (back surface) ($\mu$m) |
|---|---|---|---|---|---|
| | Front surface | Back surface | Front surface | Back surface | |
| Ex. 1 | MPC coating | UV/ozone treatment | 0.01 $\mu$g | 0.41 $\mu$g | 10 |
| Ex. 2 | MPC coating | Argon/plasma treatment | 0.01 $\mu$g | 0.40 $\mu$g | 12 |
| Ex. 3 | MPC coating | UV/ozone treatment | 0.01 $\mu$g | 0.42 $\mu$g | 10 |
| Ex. 4 | MPC coating | UV/ozone treatment | 0.01 $\mu$g | 0.47 $\mu$g | 10 |

Ex. = Example

TABLE 3

| | Method of surface treatment | | Amount of adhering fibronectin | | Thickness of adhering epithelial cells (back surface) ($\mu$m) |
|---|---|---|---|---|---|
| | Front surface | Back surface | Front surface | Back surface | |
| CEx. 1 | Not treated | Not treated | 0.15 $\mu$g | 0.15 $\mu$g | 50 |
| CEx. 2 | Argon/plasma treatment | Argon/plasma treatment | 0.40 $\mu$g | 0.40 $\mu$g | 12 |
| CEx. 3 | UV/ozone treatment | UV/ozone treatment | 0.43 $\mu$g | 0.43 $\mu$g | 11 |
| CEx. 4 | Not treated | Not treated | 0.15 $\mu$g | 0.15 $\mu$g | 55 |

CEx. = Comparative Example

INDUSTRIAL UTILITY

The intraocular lens of the present invention is an intraocular lens to be inserted after the extraction of a lens having suffered from cataract, and it characteristically inhibits secondary cataract which may occur after surgery and will have little or no fogging that may occur on the front surface side of the lens.

The invention claimed is:

1. An intraocular lens having an optic portion having a front surface and a back surface and both the front surface and the back surface are surface treated, the front surface is surface-treated to inhibit the property of adhering to a protein, and the back surface is surface-treated to improve the property of adhering to a protein, said front surface and said back surface being different from each other in the property of adhering to a protein and satisfying the relationship of the expression (x), $$PA_F < PA_B \quad (x)$$

wherein $PA_F$ is the property of adherence of said front surface to fibronectin and $PA_B$ is the property of adherence of said back surface to fibronectin in a fibronectin adherence test, wherein the optic portion is formed of one piece, wherein the front surface of the optic portion is a surface-treated front surface coated with a copolymer having a recurring unit of the general formula (I),

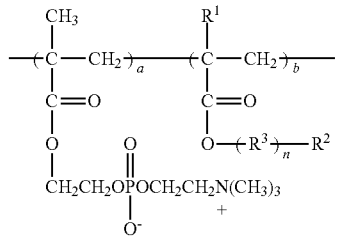

(I)

wherein $R^1$ is a hydrogen atom or an alkyl group having 1 to 4 carbon atoms, $R^2$ is a hydrogen atom, a hydroxyl group, a hydrocarbyloxy group, $-Si(OR_4)_3$ in which $R^4$ is a lower alkyl group or trimethylsilyl, or a group represented by

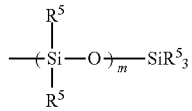

in which $R^5$ is methyl, phenyl or trimethylsiloxy and m is an integer of 1 to 100, $R^3$ is an alkylene group, a is 0.03 to 0.70, b is 0.30 to 0.97 and n is an integer of 2 or more, and having a number average molecular weight of 5,000 or more, the copolymer having been obtained from 2-methacryloyloxyethyl phosphorylcholine and (meth)acrylic ester.

2. An intraocular lens having an optic portion having a front surface and a back surface and both the front surface and the back surface are surface treated, the front surface is surface-treated to inhibit the property of adhering to a protein, and the back surface is surface-treated to improve the property of adhering to a protein, said front surface and said back surface being different from each other in the property of adhering to a protein and satisfying the relationship of the expression (x), $$PA_F < PA_B \quad (x)$$

wherein $PA_F$ is the property of adherence of said front surface to fibronectin and $PA_B$ is the property of adherence of said back surface to fibronectin in a fibronectin adherence test, wherein the optic portion is formed of one piece, wherein the front surface of the optic portion is a surface-treated front surface coated with a copolymer having a recurring unit of the general formula (I),

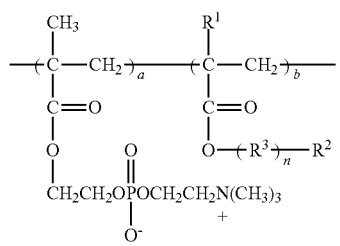
(I)

wherein $R^1$ is a hydrogen atom or an alkyl group having 1 to 4 carbon atoms, $R^2$ is a hydrogen atom, a hydroxyl group, a hydrocarbyloxy group, $—Si(OR_4)_3$ in which $R^4$ is a lower alkyl group or trimethylsilyl, or a group represented by

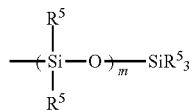

in which $R^5$ is methyl, phenyl or trimethylsiloxy and m is an integer of 1 to 100, $R^3$ is an alkylene group, a is 0.03 to 0.70, b is 0.30 to 0.97 and n is an integer of 2 or more, and having a number average molecular weight of 5,000 or more, the copolymer having been obtained from 2-methacryloyloxyethyl phosphorylcholine and (meth)acrylic ester, and the back surface of the optic portion is surface-treated by plasma treatment and/or by applying active light that works to decompose oxygen molecules to generate ozone and works to decompose said ozone to generate active oxygen in the presence of oxygen.

3. A process for producing the intraocular lens recited in claim 1, which comprises coating the front surface of an optic portion with a copolymer having a recurring unit of the general formula (I),

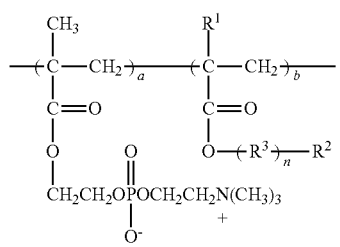
(I)

wherein $R^1$ is a hydrogen atom or an alkyl group having 1 to 4 carbon atoms, $R^2$ is a hydrogen atom, a hydroxyl group, a hydrocarbyloxy group, $—Si(OR_4)_3$ in which $R^4$ is a lower alkyl group or trimethylsilyl, or a group represented by

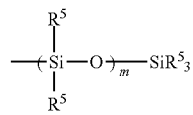

in which $R^5$ is methyl, phenyl or trimethylsiloxy and m is an integer of 1 to 100, $R^3$ is an alkylene group, a is 0.03 to 0.70, b is 0.30 to 0.97 and n is an integer of 2 or more, and having a number average molecular weight of 5,000 or more, the copolymer having been obtained from 2-methacryloyloxyethyl phosphorylcholine and (meth)acrylic ester, thereby to surface-treat the front surface of the optic portion.

4. A process for producing the intraocular lens recited in claim 2, which comprises surface-treating the front surface of an optic portion with a copolymer having a recurring unit of said general formula (I),

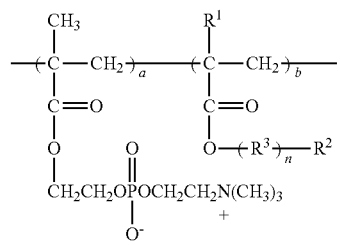
(I)

wherein $R^1$ is a hydrogen atom or an alkyl group having 1 to 4 carbon atoms, $R^2$ is a hydrogen atom, a hydroxyl group, a hydrocarbyloxy group, $—Si(OR_4)_3$ in which $R^4$ is a lower alkyl group or trimethylsilyl, or a group represented by

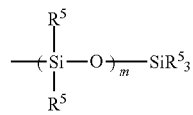

in which $R^5$ is methyl, phenyl or trimethylsiloxy and m is an integer of 1 to 100, $R^3$ is an alkylene group, a is 0.03 to 0.70, b is 0.30 to 0.97 and n is an integer of 2 or more, and having a number average molecular weight of 5,000 or more, the copolymer having been obtained from 2-methacryloyloxyethyl phosphorylcholine and (meth)acrylic ester, and surface-treating the back surface of the optic portion by plasma treatment and/or by applying active light that works to decompose oxygen molecules to generate ozone and works to decompose said ozone to generate active oxygen in the presence of oxygen.

5. A process for producing the intraocular lens recited in claim 2, which comprises surface-treating the front surface and back surface of an optic portion with a copolymer having a recurring unit of said general formula (I),

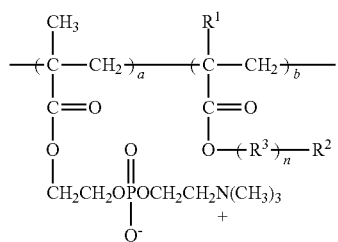
(I)

wherein $R^1$ is a hydrogen atom or an alkyl group having 1 to 4 carbon atoms, $R^2$ is a hydrogen atom, a hydroxyl group, a hydrocarbyloxy group, $-Si(OR_4)_3$ in which $R^4$ is a lower alkyl group or trimethylsilyl, or a group represented by

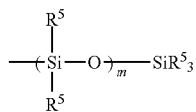

in which $R^5$ is methyl, phenyl or trimethylsiloxy and m is an integer of 1 to 100, $R^3$ is an alkylene group, a is 0.03 to 0.70, b is 0.30 to 0.97 and n is an integer of 2 or more, and having a number average molecular weight of 5,000 or more, the copolymer having been obtained from 2-methacryloyloxyethyl phosphorylcholine and (meth)acrylic ester, and surface-treating the back surface of the optic portion by plasma treatment and/or by applying active light that works to decompose oxygen molecules to generate ozone and works to decompose said ozone to generate active oxygen in the presence of oxygen.

* * * * *

UNITED STATES PATENT AND TRADEMARK OFFICE
CERTIFICATE OF CORRECTION

| | | |
|---|---|---|
| PATENT NO. | : 7,892,284 B2 | Page 1 of 1 |
| APPLICATION NO. | : 11/885221 | |
| DATED | : February 22, 2011 | |
| INVENTOR(S) | : Iwamoto | |

It is certified that error appears in the above-identified patent and that said Letters Patent is hereby corrected as shown below:

Title Page, Item (86) PCT/JP2006/001941 SHOULD BE PCT/JP2006/301941

Signed and Sealed this
Thirty-first Day of May, 2011

David J. Kappos
*Director of the United States Patent and Trademark Office*